United States Patent
Li et al.

(10) Patent No.: US 10,888,513 B2
(45) Date of Patent: Jan. 12, 2021

(54) PERSONAL CLEANSING COMPOSITIONS

(71) Applicant: Conopco, Inc., Englewood Cliffs, NJ (US)

(72) Inventors: Ningning Li, Wirral (GB); Arash Mohajer Moghadam, Wirral (GB); Joseph Muscat, Wirral (GB); Cheryl Anne Taylor, Wirral (GB)

(73) Assignee: Conopeo, Inc., Englewood Cliffs, NJ (US)

( * ) Notice: Subject to any disclaimer, the term of this patent is extended or adjusted under 35 U.S.C. 154(b) by 0 days.

(21) Appl. No.: 16/315,061

(22) PCT Filed: Jul. 3, 2017

(86) PCT No.: PCT/EP2017/066523
§ 371 (c)(1),
(2) Date: Jan. 3, 2019

(87) PCT Pub. No.: WO2018/007332
PCT Pub. Date: Jan. 11, 2018

(65) Prior Publication Data
US 2019/0231672 A1    Aug. 1, 2019

(30) Foreign Application Priority Data
Jul. 6, 2016   (EP) .................................. 16178241

(51) Int. Cl.
| A61K 8/81 | (2006.01) |
| A61K 8/06 | (2006.01) |
| A61K 8/31 | (2006.01) |
| A61K 8/73 | (2006.01) |
| A61K 8/46 | (2006.01) |
| A61K 8/92 | (2006.01) |
| A61K 8/44 | (2006.01) |
| A61Q 5/02 | (2006.01) |
| A61Q 5/12 | (2006.01) |
| A61Q 19/10 | (2006.01) |

(52) U.S. Cl.
CPC ............ *A61K 8/8158* (2013.01); *A61K 8/068* (2013.01); *A61K 8/31* (2013.01); *A61K 8/442* (2013.01); *A61K 8/463* (2013.01); *A61K 8/737* (2013.01); *A61K 8/92* (2013.01); *A61Q 5/02* (2013.01); *A61Q 5/12* (2013.01); *A61Q 19/10* (2013.01); *A61K 2800/5426* (2013.01); *A61K 2800/594* (2013.01)

(58) Field of Classification Search
None
See application file for complete search history.

(56) References Cited

U.S. PATENT DOCUMENTS

| 2004/0234483 A1 | 11/2004 | Peffly et al. | |
| 2007/0280976 A1 | 12/2007 | Taylor et al. | |
| 2009/0197784 A1* | 8/2009 | Ainger | A61K 8/463 510/127 |
| 2011/0002868 A1 | 1/2011 | Bierganns et al. | |
| 2011/0048449 A1* | 3/2011 | Hutton, III | A61K 8/342 132/221 |
| 2012/0076747 A1 | 3/2012 | Bierganns et al. | |
| 2012/0276210 A1 | 11/2012 | Dihora et al. | |
| 2016/0045417 A1 | 2/2016 | Schroeder et al. | |
| 2018/0015009 A1 | 1/2018 | Soubiran et al. | |

FOREIGN PATENT DOCUMENTS

| EP | EP3481363 | 4/2020 |
| WO | WO2007065537 | 6/2007 |
| WO | WO2008037609 | 4/2008 |
| WO | WO2012110387 | 8/2012 |
| WO | WO2013122861 | 8/2013 |
| WO | WO2015082241 | 6/2015 |
| WO | WO2016085707 | 6/2016 |
| WO | WO2017001385 | 1/2017 |
| WO | WO2017071915 | 4/2017 |
| WO | WO2017071915 | 5/2017 |
| WO | WO2018007332 | 1/2018 |

OTHER PUBLICATIONS

Search Report in EP16178241; dated Sep. 16, 2016.
Search Report and Written Opinion in PCTEP2017066523; dated Oct. 26, 2017.
Search Report and Written Opinion in EP17195899; dated Dec. 1, 2017.
Ashland; Fragrance Retention, Release and Sensory Perception from Surfactant-Rich Rinse-Off Cosmetics; Kirk-Othmer Chemical Technology of Cosmetics; Jan. 1, 2012; pp. 1-27; XP55426379.
Search Report and Written Opinion in EP17209538; dated Apr. 19, 2018.
Search Report and Written Opinion in PCTEP2018075450; dated Oct. 25, 2018.
Search Report and Written Opinion in PCTEP2018085074; dated Jan. 29, 2019.
Search Report in EP19181766; dated Jan. 15, 2020; European Patent Office (EPO).
Search Report in EP19178752; dated Dec. 4, 2019; European Patent Office (EPO).
Anonymous; Database GNPD [online] ; Damage Repair Shampoo XP055642900; Mar. 26, 2015; database accession No. 3068005.
Brenntag Specialties, Inc.; Formularies ; Hair Care Kits CASSC Suppliers Day 2015; May 1, 2015; retrieved from internet; retrieved on Nov. 15, 2019; BSI Cosmetic Ingredients.

(Continued)

*Primary Examiner* — Sin J Lee
(74) *Attorney, Agent, or Firm* — Foley & Lardner LLP

(57) ABSTRACT

The invention provides a personal cleansing composition comprising: (i) an aqueous continuous phase including cleansing surfactant; (ii) one or more oily liquid conditioning agents for skin and/or hair wherein the agent is solubilized in wormlike micelles in the aqueous continuous phase via the incorporation of at least one inorganic electrolyte and at least one linker molecule; (iii) one or more cationic deposition polymers which are selected from cationic polygalactomannans having a mean charge density at pH7 from 0.2 to 2 meq per 10 gram; and (iv) a hair substantive cationic conditioning polymer which is a homopolymer of (3-acrylamidopropyl) trimethyl ammonium chloride.

3 Claims, No Drawings

(56) References Cited

OTHER PUBLICATIONS

Search Report and Written Opinoin in EP19181752; dated Jan. 9, 2020; European Patent Office (EPO).
Written Opinion in EP16178241; dated Sep. 16, 2016; European Patent Office (EPO).
IPRP1 in PCTEP2017066523; dated Jan. 8, 2019; World Intellectual Property Org. (WIPO).
Written Opinion in EP19178752; dated Dec. 4, 2019; European Patent Office (EPO).
Search Report and Written Opinion in PCTEP2020065443; dated Aug. 17, 2020; World Intellectual Property Org. (WIPO).
Written Opinion in EP19181766; dated Jan. 15, 2020; European Patent Office (EPO).

* cited by examiner

PERSONAL CLEANSING COMPOSITIONS

CROSS REFERENCE TO RELATED APPLICATIONS

The present application is a U.S. National Phase Application under 35 U.S.C. § 371 of International Application No. PCT/EP2017/066523, filed on Jul. 3, 2017, which claims priority to European patent application No. 16178241.2 filed on Jul. 6, 2016, the contents of which are incorporated herein in their entireties.

FIELD OF THE INVENTION

The present invention relates to personal cleansing compositions such as liquid soaps, body washes and shampoos.

BACKGROUND OF THE INVENTION

In order to provide skin and/or hair conditioning benefits in a cleansing base such as a liquid soap, body wash or shampoo, it has been proposed to include beneficial oils. Oils can confer a number of skin benefits to personal washing products, which include improvements in after-wash tightness, dryness, irritancy, moisturisation and skin feel. Oils can also act as a non-greasy lubricant for hair, help in detangling hair, and can form a barrier on the hair surface to protect the cuticle and create a smooth, fly-away free look.

Since shampoo is a "rinse-off" product, the level of oil deposited on hair can be low. However, incorporation of higher levels of oil into the product is not always possible. Higher levels of oil may impair certain product properties, such as foaming ability during consumer use.

The present invention addresses this problem.

SUMMARY OF THE INVENTION

The present invention provides a personal cleansing composition comprising:
(i) an aqueous continuous phase including cleansing surfactant;
(ii) one or more oily liquid conditioning agents for skin and/or hair wherein the agent is solubilized in wormlike micelles in the aqueous continuous phase via the incorporation of at least one inorganic electrolyte and at least one linker molecule;
(iii) one or more cationic deposition polymers which are selected from cationic polygalactomannans having a mean charge density at pH7 from 0.2 to 2 meq per gram; and
(iv) a hair substantive cationic conditioning polymer which is a homopolymer of (3-acrylamidopropyl) trimethyl ammonium chloride.

DETAILED DESCRIPTION AND PREFERRED EMBODIMENTS

As used herein, the term "aqueous continuous phase" is meant a continuous phase which has water as its basis.

Suitably, the composition of the invention will comprise from about 50 to about 90%, preferably from about 55 to about 85%, more preferably from about 60 to about 85%, most preferably from about 65 to about 83% water (by weight based on the total weight of the composition).

The cleansing surfactant may suitably be selected from one or more anionic surfactants.

Typical anionic surfactants for use as cleansing surfactants in the invention include those surface active agents which contain an organic hydrophobic group with from 8 to 14 carbon atoms, preferably from 10 to 14 carbon atoms in their molecular structure; and at least one water-solubilising group which is preferably selected from sulphate, sulphonate, sarcosinate and isethionate.

Specific examples of such anionic surfactants include ammonium lauryl sulphate, ammonium laureth sulphate, trimethylamine lauryl sulphate, trimethylamine laureth sulphate, triethanolamine lauryl sulphate, trimethylethanolamine laureth sulphate, monoethanolamine lauryl sulphate, monoethanolamine laureth sulphate, diethanolamine lauryl sulphate, diethanolamine laureth sulphate, lauric monoglyceride sodium sulphate, sodium lauryl sulphate, sodium laureth sulphate, potassium lauryl sulphate, potassium laureth sulphate, sodium lauryl sarcosinate, sodium lauroyl sarcosinate, lauryl sarcosine, ammonium cocoyl sulphate, ammonium lauroyl sulphate, sodium cocoyl sulphate, sodium lauryl sulphate, potassium cocoyl sulphate, potassium lauryl sulphate, monoethanolamine cocoyl sulphate, monoethanolamine lauryl sulphate, sodium tridecyl benzene sulphonate, sodium dodecyl benzene sulphonate, sodium cocoyl isethionate and mixtures thereof.

A preferred class of anionic surfactants for use as cleansing surfactants in the invention are alkyl ether sulphates of general formula:

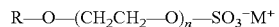

$$R-O-(CH_2CH_2-O)_n-SO_3^-M^+$$

in which R is a straight or branched chain alkyl group having 10 to 14 carbon atoms, n is a number that represents the average degree of ethoxylation and ranges from 1 to 5, preferably from 1 to 3.5, and M is an alkali metal, ammonium or alkanolammonium cation, preferably sodium, potassium, monoethanolammonium or triethanolammonium, or a mixture thereof.

Specific examples of such preferred anionic surfactants include the sodium, potassium, ammonium or ethanolamine salts of $C_{10}$ to $C_{12}$ alkyl sulphates and $C_{10}$ to $C_{12}$ alkyl ether sulphates (for example sodium lauryl ether sulphate (nEO) in which n ranges from 1 to 3.5).

Mixtures of any of the above described materials may also be used.

In a typical composition of the invention the level of cleansing surfactant will generally range from 5 to 26%, and preferably ranges from 10 to 14% (by weight based on the total weight of the composition).

In a particularly preferred composition of the invention the cleansing surfactant is sodium lauryl ether sulphate (nEO) in which n ranges from 1 to 3.5, at a level of from 10 to 14% (by weight based on the total weight of the composition).

The composition of the invention includes one or more one or more solubilised oily liquid conditioning agents (ii) for skin and/or hair.

For the purposes of the present invention, the term "oil" means a non-aqueous compound which is immiscible with water (distilled or equivalent) at a concentration of 0.1 wt %, at 25° C. The term "oily liquid" means an oil that is capable of flowing under its own weight under ambient conditions (1 atmosphere, 25° C.).

Oily liquid conditioning agents (ii) suitable for use in the invention will generally have a kinematic viscosity at 40° C. of 1000 cS ($mm^2 \cdot s^{-1}$) or less, preferably 500 cS ($mm^2 \cdot s^{-1}$) or less, more preferably 50 cS ($mm^2 \cdot s^{-1}$) or less, and most preferably 10 cS ($mm^2 \cdot s^{-1}$) or less, such as from 0.5 to 10 cS ($mm^2 \cdot s^{-1}$).

Suitable oily liquid conditioning agents (ii) for use in the invention may generally be selected from cosmetically acceptable oils such as silicone oils, hydrocarbon-based oils and mixtures thereof.

For the purposes of the present invention, the term "silicone oil" means an oil which contains at least one silicon atom, and more particularly at least one Si—O group. The term "hydrocarbon-based oil" means an oil formed from carbon and hydrogen atoms, and optionally oxygen and nitrogen atoms, and not containing any silicon or fluorine atoms. It may contain alcohol, ester, ether, carboxylic acid, amine and/or amide groups. These oils may be of plant, mineral or synthetic origin.

Examples of suitable silicone oils for use in the invention include linear or cyclic silicone oils having a kinematic viscosity of from about 0.65 to about 50, preferably from about 1.5 to about 5 cS (mm$^2 \cdot$s$^{-1}$) at 25° C. Example of such materials include linear or cyclic polydimethylsiloxanes having from 2 to 7 siloxane units, such as octamethylcyclotetrasiloxane, decamethylcyclopentasiloxane, dodecamethylcyclohexasiloxane, octamethyltrisiloxane, hexamethyldisiloxane, decamethyltetrasiloxane, dodecamethylpentasiloxane and their mixtures. Preferred are linear polydimethylsiloxanes having from 3 to 5 siloxane units and their mixtures. Such materials are commercially available for example as Dow Corning® 200 series fluids. Preferred oily liquid conditioning agents (ii) for use in the invention are generally selected from hydrocarbon-based oils.

Examples of such materials include oily liquid hydrocarbons such as $C_4$-$C_{50}$ straight or branched chain, saturated or unsaturated aliphatic or cycloaliphatic hydrocarbons and mixtures thereof. Straight chain hydrocarbons will preferably contain from about 12 to about 30 carbon atoms. Branched chain hydrocarbons can and typically may contain higher numbers of carbon atoms. Also suitable are polymeric hydrocarbons, such as polymers of $C_{2-6}$ alkenyl monomers (e.g. polyisobutene, polybutene) and poly α-olefin oils derived from 1-alkene monomers having from about 6 to about 16 carbons, preferably from about 6 to about 12 carbon atoms (e.g. polymers derived from 1-octene, 1-decene, 1-dodecene, 1-tetradecene, 1-hexadecene, and mixtures thereof). Polymeric hydrocarbons for use in the invention can be straight or branched chain polymers, and may be hydrogenated. The number average molecular weight of such polymeric materials can vary widely, but will typically range from about 200 up to about 3000.

Preferred oily liquid hydrocarbons for use in the invention include mineral oils. The term "mineral oil" in the context of this invention generally denotes an oily liquid mixture of saturated hydrocarbons with boiling-points greater than 200° C., and which is obtained from petroleum (i.e. a mineral source). Mineral oil saturated hydrocarbons include straight chain (paraffinic), branched chain (isoparaffinic) and cyclic (naphthenic) structures, and molecules containing all three configurations, with the number of carbon atoms per hydrocarbon molecule generally ranging from about $C_{15}$ to about $C_{50}$. Mineral oils suitable for use in the invention are typically obtained from petroleum through various refining steps (e.g. distillation, extraction and/or crystallisation) and subsequent purification (e.g. acid treatment and/or catalytic hydrotreatment).

Mineral oils may also be characterised in terms of their viscosity. "Light" mineral oils will generally have a kinematic viscosity of about 34 cS (mm$^2 \cdot$s$^{-1}$) or less at 40° C. and "heavy" mineral oils will generally have a kinematic viscosity ranging from about 35 cS (mm$^2 \cdot$s$^{-1}$) up to about 240 cS (mm$^2 \cdot$s$^{-1}$) at 40° C.

Light mineral oils (as defined above) are preferred for use in the invention. More preferably such light mineral oils have a kinematic viscosity of about 10 cS (mm$^2 \cdot$s$^{-1}$) or less at 40° C. Most preferably the kinematic viscosity ranges from about 3 to about 5 cS (mm$^2 \cdot$s$^{-1}$) at 40° C. Materials of this type are commercially available from Sonneborn Inc. under the brand name Lytol®.

Other suitable hydrocarbon-based oils for use in the invention include oily liquid esters. Oily liquid esters for use in the invention are generally characterised by having at least 10 carbon atoms, and may be either straight-chained or branched. The esters may have hydrocarbyl chains derived from fatty acids or alcohols (e.g. monoesters, polyhydric alcohol esters, and di- and tri-carboxylic acid esters). The hydrocarbyl radicals may include or have covalently bonded thereto other compatible functionalities, such as amides and alkoxy moieties, such as ethoxy or ether linkages.

Examples of Oily Liquid Esters for Use in the Invention Include:

aliphatic monohydric alcohol esters such as $C_5$-$C_{22}$ straight or branched-chain, saturated or unsaturated alkyl esters of $C_1$-$C_{18}$ straight or branched-chain, saturated or unsaturated alkyl alcohols (provided that the total number of carbon atoms in the ester is at least 10), such as isostearyl palmitate, isononyl isononanoate, myristyl propionate, isopropyl isostearate, isopropyl myristate, isopropyl palmitate, ethylhexyl palmitate, cetyl acetate, cetyl propionate, cetyl stearate, isodecyl neopentanoate, cetyl octanoate, isocetyl stearate, ethylhexyl stearate and mixtures thereof;

aliphatic polyhydric alcohol esters such as $C_5$-$C_{22}$ straight or branched-chain, saturated or unsaturated alkyl esters of $C_3$-$C_{30}$ straight or branched-chain, saturated or unsaturated polyols (provided that the total number of carbon atoms in the ester is at least 10), such as propylene glycol dipelargonate, pentaerythrityl tetraoctanoate, trimethylolpropane tricaprylate/tricaprate, trioctanoin, pentaerythrityl tetrapelargonate, sorbitan trioleate, caprylic/capric triglyceride, neopentyl alcohol tetraoctanoate, and mixtures thereof;

aliphatic polycarboxylic acid polyesters such as $C_5$-$C_{22}$ straight or branched-chain, saturated or unsaturated alkyl diesters of $C_2$-$C_{10}$ straight or branched-chain, saturated or unsaturated dicarboxylic acids (provided that the total number of carbon atoms in the ester is at least 10), such as diisopropyl adipate, dioctyl sebacate, dioctyl succinate, dioctyl maleate, diisostearyl adipate, diethyl sebacate, diisostearyl fumarate, dioctyl adipate and mixtures thereof; and/or $C_5$-$C_{22}$ straight or branched-chain, saturated or unsaturated alkyl triesters of $C_6$-$C_{10}$ straight or branched-chain, saturated or unsaturated tricarboxylic acids (provided that the total number of carbon atoms in the ester is at least 10), such as trioctyldodecyl citrate, triisostearyl citrate, triisopropyl citrate and mixtures thereof; and aliphatic esters of aromatic acids such as $C_{12}$-$C_{15}$ branched or unsaturated alkyl esters of benzoic acid.

Preferred oily liquid esters for use in the invention may be selected from the aliphatic monohydric and/or polyhydric alcohol esters which are described in more detail above.

Mixtures of any of the above-described materials may also be used.

The level of oily liquid conditioning agent (ii) in compositions of the invention depends on the particular material (s) used, but generally ranges from about 0.5 to about 3% by weight based on the total weight of the composition.

In a preferred composition according to the invention the oily liquid conditioning agent (ii) is selected from oily liquid hydrocarbons, oily liquid esters and mixtures thereof, at a level ranging from about 0.45 to about 2%, more preferably from about 0.5 to about 1.5% (by weight based on the total weight of the composition).

In a particularly preferred composition according to the invention the oily liquid conditioning agent (ii) is light mineral oil (as defined above), at a level ranging from about 0.5 to about 1.5% (by weight based on the total weight of the composition).

In a typical composition according to the invention, the oily liquid conditioning agent (ii) is solubilised in wormlike micelles in the aqueous continuous phase (i) to form a micro emulsion which is stable to phase separation. In the context of the invention, by 'solubilised' is meant the oily liquid conditioning agent (ii) is held within the wormlike micelles in the aqueous continuous phase.

"Wormlike micelles" in the context of this invention are elongated and flexible aggregates formed by the self-assembly of surfactant molecules in water. Above a threshold concentration, wormlike micelles entangle into a transient network, reminiscent of polymer solutions, and display viscoelastic properties. However, unlike a covalently bonded polymer backbone, the micelles are in a state of thermodynamic equilibrium with the solvent and are perpetually broken and reformed under Brownian fluctuations. This leads to a broad and dynamic distribution of micelle lengths which can change under an imposed shear or extensional flow.

Wormlike micelles can be fully described by a number of structural parameters, which cover a broad range of length-scales. The overall length of the micelles is referred to as the contour length L and varies between a few (e.g. about 1 to 10) nanometers up to a few (e.g. about 1 or 2) microns. Cryo-TEM provides a direct visualization of the micelles and can be used to estimate the contour length, while light and neutron scattering give a more accurate determination. Radii of wormlike micelles are typically a few (e.g. about 1 to 10) nm.

Another key structural parameter in the description of wormlike micelles is the persistence length $I_p$, the length over which the micelles are considered rigid. Although wormlike micelles can be extremely flexible and micrometres long, their large cross-section implies that on smaller length-scales (of order $I_p$) they act as rigid rods. Techniques such as rheology, light and neutron scattering and flow birefringence have been employed to estimate $I_p$, as well as simulations. Experimentally, persistence lengths from about 10 to about 40 nm have been reported in neutral systems. For charged wormlike micelles, the persistence length varies significantly with surfactant structure, counter-ion and salt concentration, but is typically a few tens of nanometers (e.g. about 30 to about 100 nm).

Preferably the oily liquid conditioning agent (ii) is solubilised in the aqueous continuous phase (i) via the incorporation of at least one inorganic electrolyte and at least one linker molecule. "Linker molecules" in the context of this invention are chemical additives used in surfactant systems that enhance the surfactant-oil or surfactant-water interactions. Lipophilic linkers segregate near the oil side of the interface close to the tails of the surfactants. The presence of the lipophilic linker extends the impact of the surfactant deeper into the oil phase and may promote additional orientation of the oil molecules. Hydrophilic linkers are surfactant-like molecules that coadsorb with the surfactant at the oil/water interface, but have a minimal interaction with the oil molecules. The adsorption of the hydrophilic linker at the oil/water interface increases the total interfacial area. The term "inorganic electrolyte" in the context of this invention denotes an inorganic salt which dissolves in water and ionizes but whose ions do not aggregate in solution as, for example, do the ions of a surface active agent which aggregate to form micelles.

In the context of the invention, suitable linker molecules may be selected from alkyl or aromatic carboxylic acid, alkyl or aromatic alcohol, $C_8$-$C_{22}$ alkyl ethoxy alcohol, $C_1$-$C_3$ alkyl esters of fatty acids, carboxyl amino acid and mixtures thereof. It is further preferred that the linker molecule has a formula of R(COOH) or R—$CH_2OH$ wherein R is an aromatic hydrocarbyl or alkyl group having from 6 to 10 carbon atoms.

Suitable linker molecules for use in the invention include benzoic acid, caprylic acid (and/or their sodium or potassium salts) and mixtures thereof.

An example of a preferred linker molecule for use in the invention is benzoic acid.

When included, the level of linker molecule in compositions of the invention preferably ranges from about 0.01 to about 1%, more preferably from about 0.02 to about 0.5% by weight based on the total weight of the composition.

Suitable inorganic electrolytes for use in the invention include metal chlorides (such as sodium chloride, potassium chloride, calcium chloride, magnesium chloride, zinc chloride, ferric chloride and aluminium chloride) and metal sulphates (such as sodium sulphate and magnesium sulphate). The inorganic electrolyte is used to assist in the solubilisation of the hydrocarbon-based oily liquid conditioning agents (ii) and to provide viscosity to the composition.

Examples of preferred inorganic electrolytes for use in the invention include sodium chloride, potassium chloride, magnesium sulphate and mixtures thereof.

Mixtures of any of the above described materials may also be suitable.

When included, the level of inorganic electrolyte in compositions of the invention generally ranges from about 1 to about 25%, preferably from about 1.5 to about 20% (by total weight inorganic electrolyte based on the total weight of the composition).

The composition of the invention may suitably have a viscosity ranging from 3,000 to 10,000 mPa·s, preferably from 4,000 to 9,000 mPa·s when measured using a Brookfield V2 viscometer (spindle RTV5, 1 minute, 20 rpm) at 30° C.

The composition of the invention may also include emulsified droplets of non-volatile silicone having a mean droplet diameter (D3,2) of 1 micrometre or less. Preferably the mean droplet diameter (D3,2) is 1 micrometre or less, more preferably 0.5 micrometre or less, and most preferably 0.25 micrometre or less.

A suitable method for measuring the mean droplet diameter (D3,2) is by laser light scattering using an instrument such as a Malvern Mastersizer.

The term "non-volatile silicone" in the context of this invention means a silicone with a vapour pressure of less than 1000 Pa at 25° C.

Suitable silicones for use in the invention include polydiorganosiloxanes, in particular polydimethylsiloxanes (dimethicones), polydimethyl siloxanes having hydroxyl end groups (dimethiconols), and amino-functional polydimethylsiloxanes (amodimethicones).

Suitable silicones preferably have a molecular weight of greater than 100,000 and more preferably a molecular weight of greater than 250,000.

All molecular weights as used herein are weight average molecular weights, unless otherwise specified.

Suitable silicones preferably have a kinematic viscosity of greater than 50,000 cS (mm$^2 \cdot$s$^{-1}$) and more preferably a kinematic viscosity of greater than 500,000 cS (mm$^2 \cdot$s$^{-1}$). Silicone kinematic viscosities in the context of this invention are measured at 25° C. and can be measured by means of a glass capillary viscometer as set out further in Dow Corning Corporate Test Method CTM004 Jul. 20, 1970.

Suitable silicones for use in the invention are available as pre-formed silicone emulsions from suppliers such as Dow Corning and GE Silicones. The use of such pre-formed silicone emulsions is preferred for ease of processing and control of silicone particle size. Such pre-formed silicone emulsions will typically additionally comprise a suitable emulsifier, and may be prepared by a chemical emulsification process such as emulsion polymerisation, or by mechanical emulsification using a high shear mixer. Preformed silicone emulsions having a mean droplet diameter (D3,2) of less than 0.15 micrometers are generally termed microemulsions.

Examples of suitable pre-formed silicone emulsions include emulsions DC2-1766, DC2-1784, DC-1785, DC-1786, DC-1788, DC-1310, DC-7123 and microemulsions DC2-1865 and DC2-1870, all available from Dow Corning. These are all emulsions/microemulsions of dimethiconol. Also suitable are amodimethicone emulsions such as DC939 (from Dow Corning) and SME253 (from GE Silicones).

Mixtures of any of the above described silicone emulsions may also be used.

When included, the amount of emulsified, non-volatile silicone in compositions of the invention may suitably range from 0.05 to 10%, preferably from 0.2 to 8% (by total weight silicone based on the total weight of the composition).

The composition of the invention includes one or more cationic deposition polymers (iii) which are selected from cationic polygalactomannans having a mean charge density at pH7 from 0.2 to 2 meq per gram. Such polymers may serve to enhance the delivery of conditioning agents from the composition to the skin and/or hair surface during consumer use, thereby improving the conditioning benefits obtained.

The term "charge density" in the context of this invention refers to the ratio of the number of positive charges on a monomeric unit of which a polymer is comprised to the molecular weight of the monomeric unit. The charge density multiplied by the polymer molecular weight determines the number of positively charged sites on a given polymer chain.

The polygalactomannans are polysaccharides composed principally of galactose and mannose units and are usually found in the endosperm of leguminous seeds, such as guar, locust bean, honey locust, flame tree, and the like. Guar flour is composed mostly of a galactomannan which is essentially a straight chain mannan with single membered galactose branches. The mannose units are linked in a 1-4-β-glycosidic linkage and the galactose branching takes place by means of a 1-6 linkage on alternate mannose units. The ratio of galactose to mannose in the guar polymer is therefore one to two.

Suitable cationic polygalactomannans (iii) for use in the invention include polygalactomannans, such as guars, and polygalactomannan derivatives, such as hydroxyalkyl guars (for example hydroxyethyl guars or hydroxypropyl guars), that have been cationically modified by chemical reaction with one or more derivatizing agents.

Derivatizing agents typically contain a reactive functional group, such as an epoxy group, a halide group, an ester group, an anhydride group or an ethylenically unsaturated group, and at least one cationic group such as a cationic nitrogen group, more typically a quaternary ammonium group. The derivatization reaction typically introduces lateral cationic groups on the polygalactomannan backbone, generally linked via ether bonds in which the oxygen atom corresponds to hydroxyl groups on the polygalactomannan backbone which have reacted.

Preferred cationic polygalactomannans (iii) for use in the invention include guar hydroxypropyltrimethylammonium chlorides.

Guar hydroxypropyltrimethylammonium chlorides for use in the invention are generally comprised of a nonionic guar gum backbone that is functionalized with ether-linked 2-hydroxypropyltrimethylammonium chloride groups, and are typically prepared by the reaction of guar gum with N-(3-chloro-2-hydroxypropyl) trimethylammonium chloride.

Cationic polygalactomannans (iii) for use in the invention (preferably guar hydroxypropyltrimethylammonium chlorides) generally have an average molecular weight (weight average molecular mass (Mw) determined by size exclusion chromatography) in the range 500,000 to 3 million g/mol, more preferably 800,000 to 2.5 million g/mol.

Cationic polygalactomannans (iii) for use in the invention generally have a charge density ranging from 0.5 to 1.8 meq/g.

Preferably the cationic polygalactomannans (iii) are selected from guar hydroxypropyltrimethylammonium chlorides having a charge density ranging from 0.5 to 1.8 meq/g (and mixtures thereof).

The cationic charge density of the polymer is suitably determined via the Kjeldahl method as described in the US Pharmacopoeia under chemical tests for nitrogen determination.

Specific examples of preferred cationic polygalactomannans (iii) are guar hydroxypropyltrimonium chlorides having a cationic charge density from 0.5 to 1.1 meq/g.

Also suitable are mixtures of cationic polygalactomannans (iii) in which one has a cationic charge density from 0.5 to 1.1 meq/g, and one has a cationic charge density from 1.1 to 1.8 meq per gram.

Specific examples of preferred mixtures of cationic polygalactomannans (iii) are mixtures of guar hydroxypropyltrimonium chlorides in which one has a cationic charge density from 0.5 to 1.1 meq/g, and one has a cationic charge density from 1.1 to 1.8 meq per gram.

Cationic polygalactomannans (iii) for use in the invention are commercially available from Rhodia as JAGUAR® C13S, JAGUAR® C14 and JAGUAR® C17.

In a typical composition according to the invention the level of cationic polygalactomannans (iii) will generally range from 0.05 to 0.25%, and preferably ranges from 0.15 to 0.2% by weight based on the total weight of the composition.

In a preferred composition according to the invention the cationic polygalactomannans (iii) are selected from guar hydroxypropyltrimethylammonium chlorides having a charge density ranging from 0.5 to 1.8 meq/g (and mixtures thereof), at a level ranging from 0.15 to 0.2% by weight based on the total weight of the composition.

The composition of the invention preferably includes one or more amphoteric surfactants. Suitable amphoteric surfactants are betaines, such as those having the general formula $R(CH_3)_2N^+CH_2COO^-$, where R is an alkyl or alkylamidoalkyl group, the alkyl group preferably having 10 to 16 carbon atoms. Particularly suitable betaines are oleyl betaine, caprylamidopropyl betaine, lauramidopropyl betaine, isostearylamidopropyl betaine, and cocoamidopropyl betaine.

When included, the total level of amphoteric surfactant is generally from 0.1% to 20%, preferably from 1% to 10%, more preferably from 1% to 5% by weight based on the total weight of the composition.

The composition of the invention preferably includes one or more suspending agents. Suitable suspending agents include polyacrylic acids, cross-linked polymers of acrylic acid, copolymers of acrylic acid with a hydrophobic monomer, copolymers of carboxylic acid-containing monomers and acrylic esters, cross-linked copolymers of acrylic acid and acrylate esters, heteropolysaccharide gums and crystalline long chain acyl derivatives.

Mixtures of any of the above suspending agents may be used. Preferred is a mixture of cross-linked polymer of acrylic acid and crystalline long chain acyl derivative.

When included, the total level of suspending agent is generally 0.1 to 10%, preferably from 0.5 to 6%, more preferably from 0.9 to 4% by weight based on the total weight of the composition.

The composition of the invention includes a hair substantive cationic conditioning polymer (iv) which is a homopolymer of (3-acrylamidopropyl) trimethyl ammonium chloride.

WO2013/122861 describes the synthesis of (3-acrylamidopropyl) trimethyl ammonium chloride (APTAC) homopolymers of varying molecular weights, using a radical polymerisation reaction. According to the described method, APTAC monomer is polymerised in an aqueous medium by a discontinuous adiabatic process using an azo or persulfate radical initiator. The APTAC homopolymers so obtained have molecular weights ranging from about 100,000 g/mol to about 1,000,000 g/mol. The molecular weight can be determined by using standard analytical measurements, such as size exclusion chromatography (SEC).

A polymer (iv) suitable for use in the invention is commercially available from Ashland, Inc. as N-DurHance™ A-1000 Conditioning Polymer (supplied as a 20% a.i. aqueous solution of the polymer (iv)).

In a typical composition according to the invention the level of polymer (iv) (per se as active ingredient) generally ranges from about 0.1 to about 2% and preferably ranges from about 0.2 to about 1.5% (by weight based on the total weight of the composition).

The composition of the invention preferably includes one or more ingredients that on topical application to hair are able to penetrate the hair fibre and improve fibre properties such as strength and flexibility. Such materials include molecules which can reinforce native hair fibre proteins and which are sufficiently small to penetrate the intact hair cuticle on topical application. The term "sufficiently small" in this context means smaller than about 1000 daltons (Da), preferably less than about 750 Da, more preferably less than about 500 Da, and most preferably less than about 250 Da. Specific examples include aliphatic carboxylic acids having a molecular weight from about 50 to about 200 Da and also containing at least one hydroxy or amino group, such as tartaric (2,3-dihydroxybutanedioic) acid, arginine and betaine (trimethylglycine).

A preferred composition according to the invention includes tartaric acid at a level ranging from about 0.5 to about 1.5% (by weight based on the total weight of the composition).

A composition according to the invention may contain further optional ingredients to enhance performance and/or consumer acceptability. Examples of such ingredients include fragrance, dyes and pigments and pH adjusting agents. Each of these ingredients will be present in an amount effective to accomplish its purpose. Generally, these optional ingredients are included individually at a level of up to 5% by weight based on the total weight of the composition.

The pH of the composition of the invention suitably ranges from 3.0 to 7.0, and preferably ranges from 3.0 to 6.5, more preferably from 4 to 5.1.

The composition of the invention is primarily intended for topical application to the body, preferably the hair and scalp.

Most preferably the composition of the invention is topically applied to the hair and then massaged into the hair and scalp. The composition is then rinsed off the hair and scalp with water prior to drying the hair.

The invention will be further illustrated by the following, non-limiting Examples.

EXAMPLES

Hair cleansing shampoo formulations were prepared, having ingredients as shown in Table 1. Comparative Examples (not according to the invention) are indicated by letter; Examples according to the invention are indicated by number. All weight percentages (wt %) quoted are by weight based on total weight unless otherwise stated.

TABLE 1

| Ingredient | Control | Ex. A | Ex. 1 | Ex. 2 | Ex. B | Ex. C |
|---|---|---|---|---|---|---|
| | | | wt % | | | |
| Sodium laureth sulphate (1EO) | 12 | 12 | 12 | 12 | 12 | 12 |
| Cocamidopropyl betaine | 1.6 | 1.6 | 1.6 | 1.6 | 1.6 | 1.6 |
| Guar hydroxypropyl trimonium chloride | 0.2 | 0.2 | 0.2 | 0.2 | 0.2 | 0.2 |
| Dimethiconol* | 1 | 1 | 1 | 1 | 1 | 1 |
| Carbomer | 0.4 | 0.4 | 0.4 | 0.4 | 0.4 | 0.4 |
| Ethylene glycol distearate | 0.6 | 0.6 | 0.6 | 0.6 | 0.6 | 0.6 |
| Disodium EDTA | 0.1 | 0.1 | 0.1 | 0.1 | 0.1 | 0.1 |
| Lytol ® mineral oil | — | 1 | 1 | 1 | 1 | 1 |
| Tartaric acid | — | — | — | — | — | 1 |
| Polyquaternium-10 | — | — | — | — | 1 | — |
| Polyquaternium-55 | — | — | — | — | — | 1 |

TABLE 1-continued

| Ingredient | Control | Ex. A | Ex. 1 | Ex. 2 | Ex. B | Ex. C |
|---|---|---|---|---|---|---|
| | | | wt % | | | |
| PolyAPTAC homopolymer (20% a.i.)** | — | — | 5 | 1 | — | — |
| Mica | 0.2 | 0.2 | 0.2 | 0.2 | 0.2 | 0.2 |
| Sodium hydroxide | 0.2 | 0.2 | 0.2 | 0.2 | 0.2 | 0.2 |
| Citric acid | 0.5 | 0.5 | 0.5 | 0.5 | 0.5 | 0.5 |
| Sodium benzoate | 0.5 | 0.5 | 0.5 | 0.5 | 0.5 | 0.5 |
| Sodium chloride | 0.4 | 2.5 | 2.2 | 2.2 | 2.2 | 2.2 |
| Water, perfume | to 100% | to 100% | to 100% | to 100% | to 100% | to 100% |

*Emulsion of dimethiconol with anionic emulsifier, average particle size < 1 micron (ex Dow Corning)
**N-DurHance ™ A-1000 conditioning polymer (ex Ashland Inc.)

Formulations described in Table 1 were assessed for the volume of foam generated during a typical hair washing protocol on switches of virgin dark brown European (DBE) hair, and also switches of twice-bleached hair. Four replicas were produced for each test formulation. The average of measured foam volume is shown in Table 2.

TABLE 2

| Formulation | Hair type | Average foam volume (ml) | s.d. |
|---|---|---|---|
| Control | Virgin | 103.2 | 3.9 |
| Example A | Virgin | 75.5 | 7.8 |
| Example 1 | Virgin | 115.5 | 17.2 |
| Control | Twice-bleached | 96.0 | 2.5 |
| Example A | Twice-bleached | 84.3 | 4.5 |
| Example 1 | Twice-bleached | 99.3 | 7.3 |

It can be seen from the results that the inclusion of Lytol® mineral oil (Example A) significantly reduces foam compared to the control shampoo. However, the addition of PolyAPTAC homopolymer in the formulation according to the invention (Example 1) boosts the foaming performance of the shampoo, bringing it up to parity with the control shampoo.

In a further series of foam tests, formulations described in Table 1 were assessed for the volume of foam generated during a typical hair washing protocol on switches of virgin dark brown European (DBE) hair. Three replicas were produced for each test formulation. The average of measured foam volume is shown in Table 3.

TABLE 3

| Formulation | Average foam volume (ml) | s.d. |
|---|---|---|
| Example A | 87.7 | 0.6 |
| Example 2 | 106.8 | 6.0 |
| Example 1 | 112.2 | 6.5 |
| Example B | 85.0 | 4.3 |
| Example C | 93.8 | 4.1 |

It can be seen from the results that PolyAPTAC homopolymer is also effective to boost foam when added at a level of 0.2 wt % (Example 2). However, when the PolyAPTAC homopolymer is substituted with Polyquaternium-10 (Example B) or Polyquaternium-55 & 1 wt % tartaric acid (Example C), there is no statistically significant improvement in foaming performance.

The invention claimed is:

1. A personal cleansing composition comprising:
   (i) an aqueous continuous phase comprising sodium lauryl ether sulphate (nEO) in which n ranges from 1 to 3.5;
   (ii) one or more oily liquid conditioning agents for skin and/or hair wherein the one or more agents are solubilized in wormlike micelles in the aqueous continuous phase via the incorporation of at least one inorganic electrolyte and at least one linker molecule, wherein the one or more oily liquid conditioning agents are light mineral oils, and the at least one linker molecule is selected from the group consisting of alkyl or aromatic carboxylic acid, alkyl or aromatic alcohol, $C_8$-$C_{22}$ alkyl ethoxy alcohol, $C_1$-$C_3$ alkyl esters of fatty acids, carboxyl amino acid, and a combination of two or more thereof;
   (iii) one or more cationic polygalactomannans having a mean charge density at pH 7 from 0.2 to 2 meq per gram, wherein the one or more cationic polygalactomannans comprise guar hydroxypropyltrimethylammonium chlorides; and
   (iv) a homopolymer of (3-acrylamidopropyl) trimethyl ammonium chloride;
   wherein the composition comprises 10 wt % to 14 wt % of the sodium lauryl ether sulfate, 0.5 wt % to 1.5 wt % of the one or more oily liquid conditioning agents, 0.05 wt % to 0.25 wt % of the one or more cationic polygalactomannans, and 0.2 wt % to 1.5 wt % of the homopolymer of (3-acrylamidopropyl) trimethyl ammonium chloride, based on the total weight of the composition.

2. The composition according to claim 1, wherein the light mineral oils have kinematic viscosity values of 3 to 5 cS at 40° C.

3. The composition according to claim 1, wherein the guar hydroxypropyltrimethylammonium chlorides have a charge density ranging from 0.5 to 1.8 meq/g, and mixtures thereof.

* * * * *